(12) United States Patent
Aymard et al.

(10) Patent No.: US 11,976,259 B2
(45) Date of Patent: May 7, 2024

(54) METHOD FOR TREATING LIGNOCELLULOSIC BIOMASS

(71) Applicants: IFP Energies Nouvelles, Rueil-Malmaison (FR); Institut National de Recherche Pour L'Agriculture, L'Alimentation et L'Environment, Paris (FR); Agro Industries Recherche Et Developpement, Pomacle (FR)

(72) Inventors: Caroline Aymard, Lyons (FR); Larissa Perotta, Lyons (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 972 days.

(21) Appl. No.: 16/956,168

(22) PCT Filed: Dec. 4, 2018

(86) PCT No.: PCT/EP2018/083541
§ 371 (c)(1),
(2) Date: Jun. 19, 2020

(87) PCT Pub. No.: WO2019/120995
PCT Pub. Date: Jun. 27, 2019

(65) Prior Publication Data
US 2021/0130754 A1    May 6, 2021

(30) Foreign Application Priority Data

Dec. 20, 2017 (FR) .................................. 1762610

(51) Int. Cl.
*C12G 3/02* (2019.01)
*C12G 3/021* (2019.01)
(Continued)

(52) U.S. Cl.
CPC .............. *C12G 3/021* (2019.02); *C12G 3/04* (2013.01); *C12G 3/08* (2013.01); *C12M 23/40* (2013.01);
(Continued)

(58) Field of Classification Search
CPC . C12G 3/021; C12G 3/04; C12G 3/08; C12G 3/02; C12M 23/40; C12M 45/02;
(Continued)

(56) References Cited

U.S. PATENT DOCUMENTS 4,029,515 A * 6/1977 Kiminki ............... C13K 13/002
127/1
4,304,608 A   12/1981 Regnault et al.
(Continued)

FOREIGN PATENT DOCUMENTS

CH         609092 A5      2/1979
WO    2009116070 A2 *    9/2009 ............... C12P 7/10
(Continued)

OTHER PUBLICATIONS

English Translation of Aymard Patent Publication WO 2014091109A1, published Jun. 2014. (Year: 2014).*
(Continued)

*Primary Examiner* — Joseph W Drodge
(74) *Attorney, Agent, or Firm* — Millen, White, Zelano & Branigan; Ryan R. Pool (57) ABSTRACT

The invention concerns a method for treating lignocellulosic biomass, said method comprising the following steps: a, Preparing an impregnation liquor (4) containing a chemical catalyst intended to impregnate the biomass b. Introducing the crushed biomass (6) through an inlet of an impregnation reactor (5), said inlet being situated in a first impregnation area (5*a*) of said impregnation reactor that comprises two superposed areas, said first impregnation area and a second
(Continued)

so-called dewatering area (5b) above the impregnation area c. Introducing the liquor (4a) through a first liquor inlet situated in said first impregnation area (5a) of the reactor, d. Introducing said liquor (4b) into said reactor through a second liquor inlet in another area of the reactor (5d) situated below the biomass inlet in the first impregnation area (5b). The invention also concerns the facility for implementing the method.

20 Claims, 3 Drawing Sheets (51) Int. Cl.
  *C12G 3/04* (2019.01)
  *C12G 3/08* (2006.01)
  *C12M 1/00* (2006.01)
  *C12M 1/33* (2006.01)
(52) U.S. Cl.
  CPC ............ *C12M 45/02* (2013.01); *C12M 45/06* (2013.01); *C12M 45/09* (2013.01); *C12M 47/10* (2013.01)
(58) Field of Classification Search
  CPC ...... C12M 45/06; C12M 45/09; C12M 47/10; C12M 45/00; Y02E 50/10; C08H 8/00; C12P 2201/00; C08B 1/00; D21C 1/04; D21C 1/06; D21C 1/08; B01J 4/00; B01J 4/001; B01J 4/007; B01J 37/02; B01J 37/021; B01J 37/024; B01J 37/04; B01J 37/12; B01J 37/16; B01J 37/36; B01J 2219/00164; B01J 2219/00177; B01J 2219/00274; B01J 2219/0059; B01J 2219/00731; B01J 2219/0074; B01J 2219/00891
  USPC .................................... 127/23, 24, 34, 36, 37
  See application file for complete search history.

(56) References Cited

U.S. PATENT DOCUMENTS

| | | | | |
|---|---|---|---|---|
| 4,316,748 A | * | 2/1982 | Rugg | .............. C13K 1/02 127/28 |
| 4,461,648 A | * | 7/1984 | Foody | .............. D21B 1/12 435/165 |
| 5,972,118 A | * | 10/1999 | Hester | .............. C13K 1/02 425/208 |
| 8,057,639 B2 | | 11/2011 | Pschorn et al. | |
| 8,512,512 B2 | | 8/2013 | Pschorn et al. | |
| 2012/0156742 A1 | * | 6/2012 | Powell | .............. C10G 3/00 422/620 |
| 2015/0047629 A1 | * | 2/2015 | Borden | .............. C13K 1/02 127/1 |
| 2015/0176093 A1 | * | 6/2015 | Powell | ............ B01J 19/245 127/1 |
| 2017/0044329 A1 | * | 2/2017 | Kim | .............. C08H 8/00 |
| 2017/0173819 A1 | | 6/2017 | Turnbull et al. | |
| 2017/0349923 A1 | | 12/2017 | van der Meulen et al. | |
| 2018/0029896 A1 | | 2/2018 | Foody et al. | |
| 2018/0037863 A1 | * | 2/2018 | Foody | .............. D21C 3/06 |
| 2018/0258190 A1 | * | 9/2018 | Balan | .............. C12P 19/14 |
| 2018/0355303 A1 | | 12/2018 | Rowland et al. | |
| 2019/0241984 A1 | | 8/2019 | Hudebine et al. | |
| 2020/0002482 A1 | * | 1/2020 | Aymard | ............ C12M 21/12 |
| 2020/0339761 A1 | * | 10/2020 | Aymard | ............ D21C 1/10 |
| 2021/0087590 A1 | * | 3/2021 | Aymard | ............ C12P 19/02 |
| 2021/0381017 A1 | * | 12/2021 | Bouras | .............. C12P 19/14 |
| 2022/0056395 A1 | * | 2/2022 | Bouras Galinie | ...... C12M 23/58 |
| 2022/0145232 A1 | * | 5/2022 | Bouras | ............ C12M 39/00 |

FOREIGN PATENT DOCUMENTS

| | | | | |
|---|---|---|---|---|
| WO | 13141776 A1 | | 9/2013 | |
| WO | 2014091109 A1 | * | 6/2014 | ............. C13K 1/02 |
| WO | 15173226 A1 | | 11/2015 | |
| WO | 16101073 A1 | | 6/2016 | |
| WO | 17088061 A1 | | 6/2017 | |
| WO | 17136915 A1 | | 8/2017 | |
| WO | 18015227 A1 | | 1/2018 | |

OTHER PUBLICATIONS

International Search Report PCT/EP2018/083541 dated Jan. 24, 2019 (pp. 1-3).

* cited by examiner

METHOD FOR TREATING LIGNOCELLULOSIC BIOMASS

FIELD OF THE INVENTION

The invention relates to a process for treating lignocellulosic biomass for producing "second-generation" (2G) sugary juices. These sugary juices may be used to produce other products via a biochemical pathway (e.g. alcohols such as ethanol, butanol or other molecules, for example solvents such as acetone, etc.). This process generally includes three steps, which are the liquor preparation, the impregnation of the biomass and the pretreatment of the impregnated biomass, for example by cooking, optionally followed by steam explosion. The invention is more particularly focused on the first two steps of the process.

PRIOR ART

Lignocellulosic biomass represents one of the most abundant renewable resources on Earth. The substrates considered are very varied, they relate both to ligneous substrates such as various woods (hardwoods and softwoods), coproducts derived from agriculture (wheat straw, rice straw, corn cobs, etc.) or from other agrifood, paper, etc. industries.

The process for the biochemical conversion of the lignocellulosic material into 2G sugary juices notably comprises a pretreatment step and a step of enzymatic hydrolysis with an enzymatic cocktail. These processes also usually include an impregnation step before the pretreatment. The sugary juices resulting from the hydrolysis are then treated, for example by fermentation, and the process also comprises separation steps and/or a step of purification of the final product.

Lignocellulosic biomass is composed of three main polymers: cellulose (35% to 50%), which is a polysaccharide essentially constituted of hexoses; hemicellulose (20% to 30%), which is a polysaccharide essentially constituted of pentoses; and lignin (15% to 25%), which is a polymer of complex structure and of high molecular weight, composed of aromatic alcohols connected by ether bonds. These various molecules are responsible for the intrinsic properties of the plant wall and organize themselves into a complex entanglement.

Among the three base polymers that make up the lignocellulosic biomass, cellulose and hemicellulose are the ones that enable the production of 2G sugary juices.

Usually, hemicellulose is predominantly broken down into sugar during the pretreatment and cellulose is converted into glucose by enzymatic hydrolysis. However, access to crude cellulose remains difficult for enzymes to access, hence the need for a pretreatment. This pretreatment makes it possible to modify the physicochemical properties of the lignocellulosic material in order to improve the accessibility of the cellulose to enzymes and its reactivity to enzymatic hydrolysis.

Numerous technologies advantageous to the invention for performing this pretreatment exist, which will be grouped hereinbelow under the generic term "cooking": acidic cooking, alkaline cooking, steam explosion, "organosolv pulping" processes. The latter process concerns pretreatment in the presence of one or more organic solvents and generally water. The solvent may be an alcohol (ethanol), an acid such as acetic acid or formic acid, or else acetone. "Organosols pulping" processes lead to at least partial dissolution of the lignin and partial dissolution of the hemicelluloses. There are thus two outlet streams: the pretreated substrate with residual cellulose, hemicellulose and lignin, and the solvent phase which contains the dissolved lignin and a portion of the hemicelluloses. There is generally a step of regeneration of the solvent which makes it possible to extract a lignin stream. Certain "organosolv pulping" treatments (notably with ethanol) are coupled with the addition of a strong acid (such as H2SO4). It may also be envisaged to place the biomass in contact with the solvent via an impregnation reactor before the cooking phase or to place the biomass in contact with the acid catalyst before performing "organosolv pulping" cooking.

Various configurations are reported, for example, in the publication "Production of bioethanol from lignocellulosic materials via the biochemical pathway: a review", M. Balat, Energy Conversion and Management 52 (2011) 858-875, or in the publication "Bioethanol production from agricultural wastes: an overview", N. Sarkar, S. Kumar Ghosh, S. Bannerjee, K. Aikat, Renewable Energy 37 (2012) 19-27.

One of the most effective pretreatments is acidic steam explosion which enables almost complete hydrolysis of hemicellulose and a significant improvement in the accessibility and reactivity of cellulose with respect to enzymes. This pretreatment may be preceded by other treatment(s).

U.S. Pat. Nos. 8,057,639 and 8,512,512 propose a process comprising a first step of hydrolysis of hemicellulose to C5 sugars under mild conditions which thus protect them from degradation. This step is performed in a first reactor at a pressure of 1.5 bar or more by injection of steam, at a temperature of 110° C. or more, and optionally in the presence of a weak acid. After this step, washing is performed in order to extract and recover the C5 sugar juices before sending the remaining biomass, enriched in cellulose and lignin, to a second step (second reactor) where the steam explosion takes place. This second reactor operates at a higher pressure than the first reactor with an injection of high-pressure steam which causes a sudden expansion of the biomass (steam explosion).

Patent application WO-2013/141776 describes, in the papermaking field, an impregnation process in a vertical reactor (impregnator) containing basic impregnation liquor, thus defining a first zone in which the impregnation is performed. The lignocellulosic material is received at the bottom of the impregnator, and it is transferred to the top of the impregnator by means of two transfer screws. During its transfer into the second zone of the impregnator located above the level of the liquid, the biomass drains and the liquid falls back into the first zone. In this configuration, the liquid level is controlled by the introduction of basic liquor.

The aim of the invention is to improve the impregnation process and the suitable equipment described in the above-mentioned application WO-2013/141776.

The invention is notably directed toward improving the quality of impregnation of biomass with a catalytic liquor.

Incidentally, the invention seeks to make the impregnation process and equipment simpler to use and/or less fluid-intensive.

SUMMARY OF THE INVENTION

The subject of the invention is firstly a process for treating a lignocellulosic biomass, said process comprising the following steps:
   a. Preparing an impregnation liquor containing a chemical catalyst intended for the impregnation of the biomass, chosen from an acid catalyst, a basic catalyst and an oxidizing catalyst, and preferably an acid catalyst b. Introducing the milled biomass via an inlet of an impregnation reactor, said inlet being located in a first impregnation zone of said impregnation reactor which comprises two superposed zones, said first impregnation zone and a second "draining" zone above the first impregnation zone
c. Introducing the liquor via a first liquor inlet located in said first impregnation zone of the reactor.

The invention is characterized in that the process also comprises the following step:

d. Introducing said liquor into said reactor via a second liquor inlet in another reactor zone located below the biomass inlet located in the first impregnation zone.

In the context of the present invention, the spatial references of the type "above" or "below" are understood as a function of the preferentially vertical or oblique orientation relative to the vertical of the reactor, which, over its height, thus comprises a succession of zones through which passes the biomass which will feed the reactor, including an introduction zone and then a draining zone. The biomass preferably undergoes an ascending motion in the reactor, the introduction zone thus being located "under" the draining zone. (The invention could be adapted to other reactor configurations, the terminology then being adapted).

The invention thus proposes to inject into the impregnation reactor the catalytic liquor not only into the impregnation zone of the reactor, which is conventional, but also under the impregnation zone, below the point of injection of the biomass into the reactor. This zone is generally considered as a "dead" or "inactive" zone of the reactor, since the biomass introduced into the first impregnation zone will be conveyed to the draining zone, above the impregnation zone, this ascending motion being brought about by transportation means in the reactor, for instance a transportation screw. This zone, generally of low height relative to the other two and which is located below the first impregnation zone, corresponds to the bottom of the reactor, generally positioned vertically or obliquely, via which bottom is (are) introduced into the reactor the transportation screw(s), the motion of which is actuated by a motor. Injecting liquor into this zone runs against the usual practices since little/no biomass resides in this zone, and if it were envisaged to inject a fluid into this zone, it would then, if at all, only be water intended, in the case of using transportation screws in the reactor, to lubricate the screws, thus for an essentially mechanical purpose.

Now, it turns out that, surprisingly, injecting catalytic liquor into this zone, under the point of injection of the biomass into the reactor, is particularly beneficial to the impregnation process. It has in point of fact been proven, indirectly, by comparative measurement of the yields on conclusion of the steam explosion pretreatment following the impregnation treatment, that the impregnation of the biomass is performed more successfully, for an equivalent consumption of catalyst (i.e. without overconsuming catalytic liquor, but by injecting it into two different zones of the reactor instead of one).

The reasons for this improved impregnation may be manifold: the liquor injected under the point of injection of the biomass could make it possible to better treat the biomass just in its injection zone. In point of fact, to inject the biomass, use may usually be made of a feed screw which compresses and conveys the biomass into the reactor, a biomass plug being formed in the downstream part of the screw which prevents any backflow of liquid to the upstream end of the screw. This plug, in addition, when it enters the reactor, opens, notably mechanically by the use of a piston which, in the reactor, goes to meet the plug under consideration. Injecting liquor just below the zone where this biomass plug splits appears to be extremely favorable to "earlier" impregnation of the biomass with the catalyst during the conveying of the biomass in the reactor, and thus to better, more complete impregnation, for an identical residence time in the reactor. In addition, it was found that the liquor thus injected perfectly replaces any washing water to lubricate the biomass transportation means in the reactor, of the screw type.

Other advantages arise from the invention: A better result is obtained, with no extra consumption of catalyst. The equipment is simplified, since, instead of providing an independent water supply at the bottom of the reactor, liquor is withdrawn from its preparation zone. Limiting the addition of water to the reactor is also advantageous for limiting the dilution of the catalytic liquor in the reactor, to therefore limit the need, if any, to readjust the catalyst content of the liquor, for example.

Advantageously, and as mentioned previously, the biomass is transported from the first impregnation zone to the second draining zone by transportation means such as one or more transportation screws. The biomass becomes impregnated with liquor in the first zone and is drained in the second zone. The transportation screw of the draining zone may be surrounded with a grate, through the orifices of which flows the excess liquid.

Advantageously also, the introduction of the biomass into the first impregnation zone of the reactor is performed by a feed means creating a biomass plug which prevents the backflow of liquid from said first zone into said feed means, said feed means notably being a feed screw.

According to the invention, the liquid originating from the same preparation zone will thus be injected into two points, and it will be possible, for a given consumption of liquor, to dose the proportion of liquor injected into the impregnation zone relative to that injected under the biomass injection point: preferably, 80% to 98%, notably 85% to 90% (by volume) of the liquor introduced into the impregnation reactor is introduced via the first liquor inlet, and the remainder to 100% of the liquor introduced into the reactor is introduced via the second liquor inlet. The majority of the liquor is thus injected into its conventional zone, "withdrawing" up to 20% of this amount to inject it into the bottom of the reactor.

The introduction of liquor via the first liquor inlet and/or via the second liquor inlet may take place continuously or discontinuously.

Preferably, the other reactor zone in which the second liquor inlet is located is an inactive zone located at the bottom of the reactor positioned substantially vertically or obliquely relative to the vertical.

According to a preferred embodiment, the liquor used is an acid catalysis liquor, and the pH of the liquor is adjusted to between 0.1 and 4, notably between 0.3 and 2.

Examples of acids that may be used include at least one acid chosen from sulfuric acid, hydrochloric acid, nitric acid and oxalic acid. Their content, in the aqueous phase, is preferably between 0.2% and 8% by weight.

A subject of the invention is also a process for the continuous treatment of a lignocellulosic biomass, comprising the steps described previously, and which continues, continuously or non-continuously, comprising the following steps:

e. Transferring the impregnated and drained biomass from the impregnation reactor outlet to a cooking reactor, optionally coupled with steam explosion f. Pretreating said biomass in said reactor
g. Enzymatic hydrolysis of the pretreated biomass
h. Alcoholic fermentation of the enzymatic hydrolysis must obtained from the pretreated biomass.

A subject of the invention is also a lignocellulosic biomass treatment facility, comprising:

A zone for preparing an impregnation liquor containing a chemical catalyst for the impregnation of the biomass, notably an acid, basic or oxidizing catalyst, and preferably an acid catalyst, and equipped with a liquor outlet An impregnation reactor comprising a first impregnation zone equipped with a biomass inlet and a second zone superposed on the first, known as the draining zone, and equipped with a biomass outlet A means for feeding milled biomass to the impregnation reactor via the biomass inlet of the reactor located in the first impregnation zone A first means for feeding impregnation liquor to the reactor connecting a liquor outlet of the liquor preparation zone to a first liquor inlet in the first impregnation zone of the reactor, such that the facility also comprises:

A second means for feeding impregnation liquor to the reactor connecting a liquor outlet of the liquor preparation zone to a second liquor inlet in a reactor zone located below the biomass inlet of the first impregnation zone.

This facility makes it possible to perform the process described previously, by providing the means for introducing the catalytic liquor into a second point of the impregnation reactor.

It should be noted that the invention also includes the injection of catalytic liquor into the impregnation reactor in addition to two injection points, for example via three or four different inlets into the reactor, including at least one, for example two, in the impregnation zone and at least one, for example one or two, under the biomass injection point.

The facility according to the invention preferably uses an impregnation reactor of vertical or oblique orientation relative to the vertical, the biomass undergoing an ascending motion from the first impregnation zone to the second draining zone by means of one or more transportation screws placed in the reactor in said zones.

The impregnation liquor preparation zone may be a tank, or a static mixer or a dynamic mixer or any other means making it possible to mix a solvent (for example water) and the catalyst (for example an acid such as $H_2SO_4$ in the case of an acidic liquor).

According to a first embodiment, the first and the second liquor feed means comprise a common pipe portion connected to the same liquor outlet of the liquor preparation zone: a bypass is made on the pipe for supplying liquor to the impregnation zone of the reactor.

According to another embodiment, the first and the second liquor feed means are each connected to a different outlet of the liquor preparation zone: a completely separate pipe is then used to convey the liquor from another outlet to the second liquor inlet of the reactor.

As already mentioned, the biomass feed means is preferably designed to create a biomass plug which prevents the backflow of liquid from said first zone into said feed means, said feed means notably being a feed screw.

The facility according to the invention may also additionally comprise a reactor for pretreatment of the biomass obtained at the outlet of the impregnation reactor, an enzymatic hydrolysis reactor and an alcoholic fermentation reactor, the set of reactors, or at least two of them, being mounted in series.

A subject of the invention is also the use of the process or of the facility described previously for the treatment of biomasses such as wood, straw, agricultural residues, and all dedicated energy crops, notably annual or perennial plants such as miscanthus in order to produce sugars, biofuels or biobased molecules. More generally, the lignocellulosic biomass or lignocellulosic materials employed in the process according to the invention is obtained, for example, from raw or processed wood (hardwood and softwood), agricultural byproducts such as straw, plant fibres, forestry crops, residues from alcohol-generating, sugar-yielding and cereal-yielding plants, residues from the paper industry, marine biomass (for example cellulosic macroalgae) or cellulosic or lignocellulosic material transformation products. The lignocellulosic materials may also be biopolymers and are preferentially rich in cellulose.

Preferentially, the lignocellulosic biomass used is wood, wheat straw, wood pulp, miscanthus, rice straw or corn stalks.

DETAILED DESCRIPTION

The invention will be described in detail below with the aid of nonlimiting examples, illustrated by the following figures.

Figure 1:
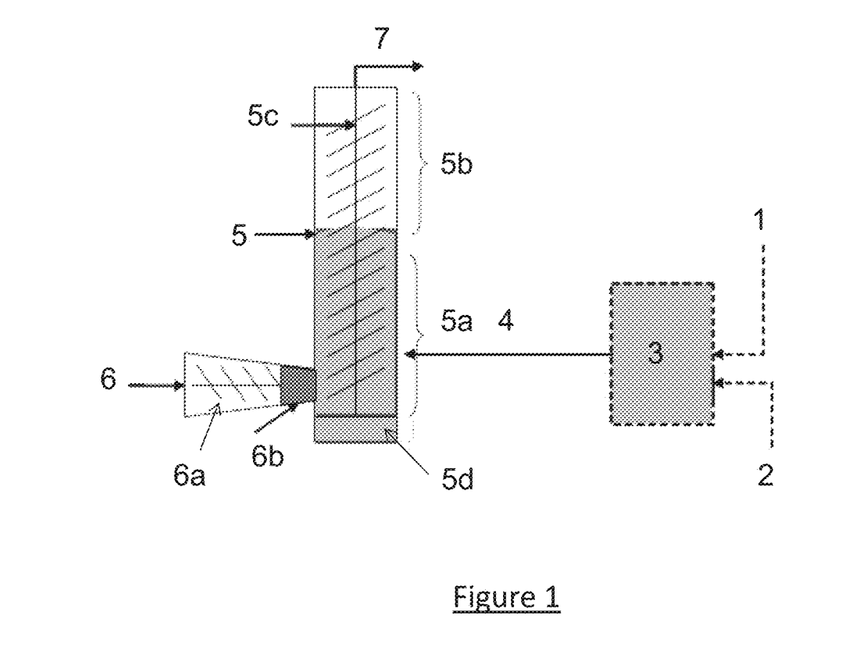
FIG. 1: a schematic representation of equipment for impregnating biomass with a liquor according to the prior art.
Figure 2:
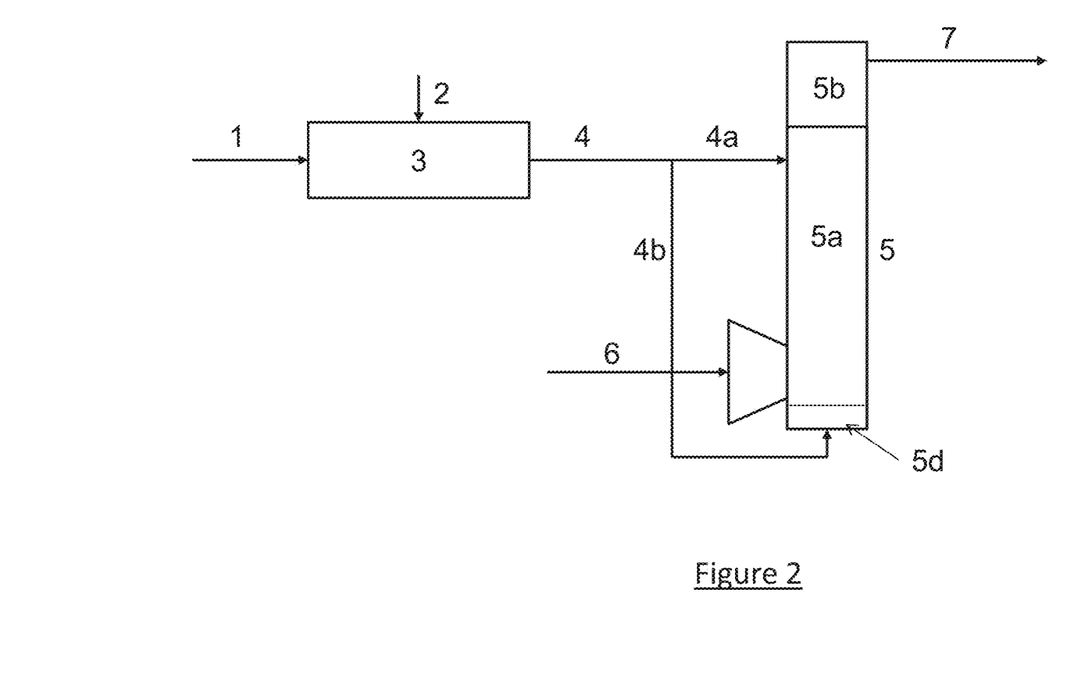
FIG. 2: a synoptic representation, of block diagram type, of the impregnation equipment and process used in the invention.
Figure 3:
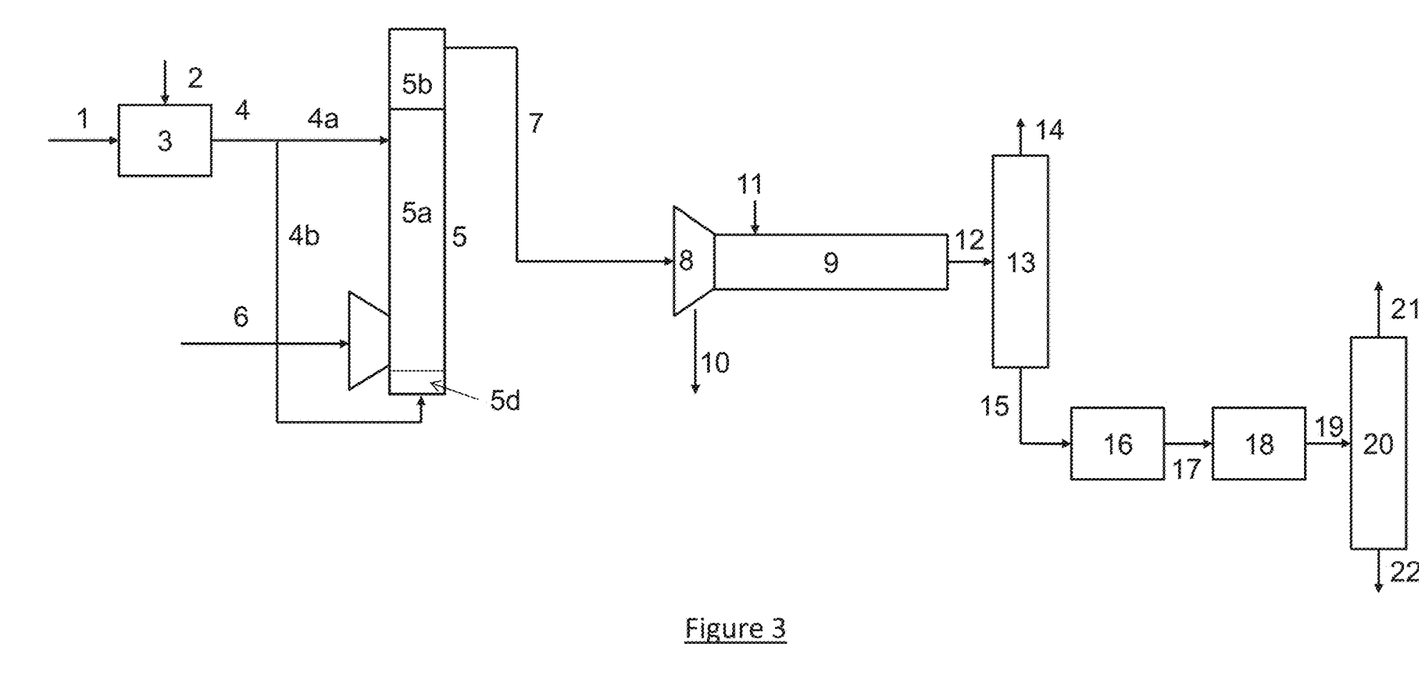
FIG. 3: a synoptic representation, of block diagram type, of the complete equipment and process from the impregnation of the biomass as represented in FIG. 2 up to the continuous conversion of the biomass into ethanol.

Description of FIGS. 1 to 3 using the following references, the same references corresponding to the same components/fluids/products in all of the figures:

1: Entry of water into the liquor preparation tank
2: Entry of acid into the liquor preparation tank
3: Liquor preparation equipment (tank)
4: Acidic liquor
4a: Acidic liquor to the impregnation equipment (reactor) (injection via the impregnation zone)
4b: Acidic liquor to the impregnation equipment (reactor) (injection into the bottom for lubrication of the conveying screws)
5: Impregnation equipment (reactor)
5a: Impregnation zone of the impregnation reactor
5b: Draining zone of the impregnation reactor
5c: Screw for transporting the biomass into the impregnation reactor
5d: impregnation reactor zone located below the impregnation zone 5a (below the point 6b for biomass entry into the reactor 5 by means of the feed screw 6a)
6: Milled biomass
6a: Conical screw for feeding biomass to the impregnation reactor
6b: biomass sealing plug in the feed screw 6a
7: Impregnated and drained biomass
8: Screw or plug-screw feeder of the pretreatment equipment 9: Pretreatment equipment (explosion reactor)
10: Press liquor of the screw 8 of the pretreatment equipment
11: Injection of steam for the pretreatment
12: Pretreated biomass and steam
13: Equipment (cyclone) for separating steam and pretreated biomass
14: Steam to condensation
15: Pretreated biomass
16: Enzymatic hydrolysis
17: Enzymatic hydrolysis must containing sugars
18: Alcoholic (ethanolic) fermentation
19: Fermentation wine containing ethanol (alcohol)
20: Distillation
21: Concentrated alcohol
22: Crude vinasses FIG. 1 is a schematic representation of equipment for impregnating biomass with a liquor according to the prior art; it is thus not necessarily to scale and does not represent all the components of the equipment, but only those that are more particularly of interest for the description of the invention.

The process according to the invention is a process for treating a lignocellulosic biomass before enzymatic hydrolysis. It is integrated into processes directed toward producing second-generation sugars from which many biochemical pathways make it possible to obtain oxygenated molecules (for example alcohols such as ethanol, butanol, etc.).

Thus, the examples that follow relate to an integrated acid impregnation process followed, continuously or discontinuously, by a steam explosion pretreatment, optionally with recycling of the acidic impregnation liquor.

This process is compatible with the processes for producing 2G sugars (i.e. those obtained from lignocellulosic biomass) or more broadly biobased molecules (i.e. molecules from natural substrates or derived from natural substrates).

The Biomass and the Transfer Zone

Depending on the biomass (straw, wood, etc.), a milling step is necessary in order to have a particle size compatible with the technological means and the operating conditions of the steps. For this, simple chipping may be sufficient but milling with or without refining may be required.

In general, the milled biomass 6 has a particle size (the largest size) of not more than 300 mm. Usually, the milling of the straw is performed with screens of from 5 to 100 mm and the wood is chipped into parallelepipedal chips with a length of between 20 and 160 mm, a width of between 10 and 100 mm and a thickness of between 2 and 20 mm.

The milled biomass 6 is brought to the first impregnation zone 5a of the impregnation reactor via a conical feed screw 6a in which a hermetic biomass plug 6b prevents the backflow of liquid from said zone 5a into the screw 6a, just before entry into the first impregnation zone. This conical compression screw may comprise a cowling in the form of a perforated grate. It has a conical-shaped part, said conical part being connected to the bottom of the first impregnation zone 5a of the reactor. This screw 6a thus performs a dual role: firstly, the introduction of the biomass continuously into the impregnation reactor, and secondly, the formation of a plug in order to achieve leak tightness and prevent leakage of liquor from the impregnation reactor to the screw and upstream of the screw.

Impregnation Step

The impregnation is performed at atmospheric pressure and at a temperature of 10-95° C. The residence time of the biomass in the impregnation reactor 5 is customarily from 20 seconds to 60 minutes, preferably at least 30 seconds, preferably at least 1 minute, preferably not more than 45 minutes, and usually between 1 and 35 minutes. Preferably, it is performed in a single reactor.

The impregnation reactor 5 (or impregnator) is of tubular shape and of vertical or inclined orientation with an angle of less than 60° with respect to the vertical. It is vertical in the examples. This reactor includes two superposed impregnation zones 5a,5b that are located on the same axis. The lower zone 5a is known as the first impregnation zone and receives, via an aperture, the pressed biomass coming from the feed screw 6a, above which aperture is provided an acidic liquor inlet 4 still in this first zone 5a. The zone 5b located above (top zone) is known as the second impregnation zone, or draining zone: it receives the biomass coming from the first impregnation zone 5a.

The reactor 5 (impregnator) is equipped with one or more transportation screws 5c which transfer the biomass via the bottom of the first impregnation zone to the outlet aperture via the top of the second impregnation zone 5b.

The first impregnation zone 5a (therefore the zone where the impregnation takes place) corresponds to the space filled with the impregnation liquor. The second impregnation zone 5b does not contain any continuous liquid phase. It is particularly advantageous to maintain a constant distribution between the first impregnation zone and the second impregnation zone. To do this, the reactor is equipped with a detection system (level sensor), preferably with a system for regulating the level of liquor (not shown), which makes it possible to ensure filling to the desired level.

The catalytic impregnation liquor is an aqueous solution with a pH of from 0.1 to 6, preferably from 0.2 to 4.0, and a temperature of 10-95° C. The acid is, here, sulfuric acid. This type of liquor is well known to those skilled in the art and any other acid customarily used for impregnation is suitable for use. The amount of acid and the temperature of the liquor are generally fixed. The means for obtaining and maintaining the temperature are known to those skilled in the art. The preparation of the liquor takes place here in a tank 3 with a water inlet 1 and a concentrated sulfuric acid inlet 2.

The effect of compressing the biomass during the formation of the plug (at the level of the transfer screw) and of decompressing at the inlet of the first impregnation zone filled with liquor makes it possible to better saturate the biomass (sponge effect). The biomass is transferred across the first zone 5a where it is impregnated toward the second impregnation zone 5b located above the level of the liquor.

In the second impregnation zone 5b, a portion of the impregnated liquor is separated from the impregnated biomass by draining during the rise into the second impregnation zone, the drained liquor falling back into the first impregnation zone 5a.

Preferably, the second impregnation zone 5b is equipped with screen(s) retaining the wet biomass in the second impregnation zone, which screen therefore allows the liquid to flow from the second impregnation zone 5b into the first impregnation zone 5a.

On leaving the second impregnation zone and the impregnation reactor, the impregnated and drained biomass is recovered and contains little or no free water. Its solids content generally varies between 15% and 40% by weight.

The separated liquor, often referred to as spent liquor, is found in the liquid of the first impregnation zone.

Preparation of the Impregnation Liquor

Owing to the impregnation, there is a loss of liquor and of acidity. It is therefore necessary to regularly add fresh acidic liquor.

These additions make it possible to precisely regulate the level of liquor in the impregnation reactor.

The liquor preparation is also a step that makes it possible to regulate its operating parameters, for instance the temperature, the pH or any other feature. The appropriate acid concentration is regulated by means of inputs of acid and/or water. It also makes it possible to produce a homogeneous liquor. This step is performed in a liquor preparation zone.

Various devices may be used, for example, here, a mixing tank equipped with a stirring system or a mixer, not shown (preferably a static mixer).

Preferably, the device is equipped with sensors for measuring the pH and the flow rate for the water, acid and prepared liquor, etc. All of these sensors together make it possible to put in place a control that balances the flow rates and the acidities so as to have a continuous operation that is stable under the desired conditions.

The liquor preparation tank 3 and/or the impregnation reactor 5 is (are) equipped in order to perform the heating, with heating means such as a jacket, coils (and optionally exchangers positioned on the optional liquor recirculation loop next to or directly on said devices (tank, mixer, etc.).

The liquor tank 3 is connected to the impregnation reactor via one or more liquor transportation pipes.

The liquor may thus be prepared with a suitable concentration and suitable flow rate which make it possible to obtain the determined pH (or any other feature) that may be the nominal value for the regulation.

The invention arises from the following observation: still in FIG. 1, in the impregnation reactor 5, the existence is noted of a third zone 5d located below the level of introduction of the biomass plug 6b, below the first impregnation zone 5a: this is a "dead" zone, since there is no desired passage of biomass in this place. This dead or "inactive" zone is necessary to leave space for the expansion of the plug and to limit the accumulation of solids at the bottom of the reactor. This zone 5d consists essentially of liquid, since it is located outside the desired passage for the solid. Nevertheless, on account of deviations from the ideal situation of a piston transportation by the ascending screws 5c, and of the presence of particles in the biomass plug, the possible presence of a small fraction of solids in the dead zone is observed. Now, it is desirable to avoid the accumulation of solid components in this zone 5d.

It was thus chosen to inject into this zone 5d a fluid, not a simple water supply which would bring about additional dilution of the liquor in the reactor, but an additional liquor supply coming from the preparation tank 3, represented in FIGS. 2 and 3 described below.

According to FIG. 2, the acid and the water are introduced, respectively, via pipes 1 and 2 into the acidic liquor preparation tank 3. The acidic liquor of pipe 4 is then injected into the impregnator 5 to be mixed with the milled biomass which is introduced via pipe 6 into the process. The acidic liquor 4 is injected into the impregnation tank 5, and more precisely into the impregnation zone 5a, by means of pipes 4a and 4b. The biomass—placed in contact with the acidic liquor in the impregnation zone 5a-then passes into the draining zone 5b in order to be separated from the liquid fraction. The impregnated and drained biomass is transferred via pipe 7 into the next step of the process.

In this implementation example of the invention, it was chosen to add an additional pipe 4b for supplying liquor to the zone 5d, under the biomass feed point of the reactor 5, in the form here of a bypass pipe of the main pipe 4-4a connected to an inlet of the tank 3. Needless to say, any other arrangement of pipes for also conveying liquor to the bottom of the reactor is also possible, notably by alternatively providing a dedicated pipe connecting a second outlet of the tank to the inlet at zone 5d of the reactor 5, or by using any other system for distributing liquor from the tank 3 to the two separate inlets of the reactor 5. Means for adjusting the amount of liquor to be injected into the impregnation zone 5a relative to the amount to be injected into the zone 5d are provided and known from the prior art (regulated valves, etc.).

FIG. 3 shows the process of FIG. 2, continuing beyond the impregnation by a continuous steam explosion pretreatment, and then by several other successive treatment steps up to the alcoholic fermentation.

The process thus proceeds in the following manner: the impregnation takes place as in FIG. 2 in the reactor 5, and will thus not be described again.

Once it has been impregnated and drained, the biomass is transferred via pipe 7 and introduced into the steam explosion pretreatment unit 9 by means of a transportation screw 8 which makes it possible to compress the biomass to form a biomass plug. During this compression, a solid/liquid separation takes place, and the spent acidic liquor 10 is evacuated through the perforated zone of the screw. Optionally, this spent acidic liquor 10, also known as the press liquor, may be at least partly recycled by reintroducing it into the liquor preparation tank 3. The biomass is then treated in the treatment equipment 9. Steam is introduced via pipe 11 into the pretreatment reactor 9. Acidic cooking coupled with steam explosion is performed in this reactor. An explosive expansion output takes place and the mixture of pretreated substrate and steam 12 is sent to separation equipment of cyclone type 13.

It should be noted that, in this example, the cooking is followed by steam explosion, but the steam explosion remains optional, and that treatments other than cooking are possible for achieving the objective of this pretreatment, namely modifications of at least one physicochemical property of the (impregnated) biomass, such as its degree of polymerization or its crystallinity. These other cooking treatments have been mentioned above. The operating conditions of the cooking, which is acidic here, are, for example, the following: the equipment 9 comprises a cooking zone, in which the biomass is placed in contact for 1-30 minutes with steam with a specific steam consumption of 0.05-10 tonnes/tonne of biomass solids, said zone being at a temperature of 150-250° C. and a pressure of 0.5-4 MPa, and then a zone for expansion of the biomass obtained from the cooking zone, followed by a zone for separating the steam from the biomass. Preferably, the conditions are regulated so that the cooking time is limited to 1-30 minutes. Generally, the specific steam consumption is 0.05-10 tonnes/tonne of solids. The steam recovered is advantageously recycled after compression into the steam explosion step, or optionally is recycled into the utilities of the site. Here, this step is performed in a reactor 9 which is tubular and horizontal (which may also be slightly inclined for flow of the liquid), and which is equipped with a biomass transfer screw. At the downstream end of the reactor 9, the biomass is entrained very rapidly by the steam to an expansion zone in a line referred to as a blowline, which has a reduced diameter relative to the cooking zone.

In the equipment 13, the steam 14 is separated from the pretreated biomass 15. The pretreated biomass is then transformed in the transformation tool 16 into a must 17 containing sugars, using an enzymatic cocktail. The sugars are converted into alcohol (e.g.: ethanol, acetone, butanol) by fermentation in the fermentation step 18. The fermentation wine 19 is sent to a separation and purification step 20. Step 20, which is performed, for example, by distillation, allows the separation of a stream 21 containing the concentrated alcohol from the crude vinasses (spend water, residual lignin) 22. The conditions of the enzymatic hydrolysis and of the consecutive or simultaneous fermentation are suitable for the desired products and are known to those skilled in the art.

It should be noted that, as for FIG. 2, the invention applies similarly and with the same advantages to a process in which some or all of the steps following the steam explosion take place not continuously but in "batch" or "fed batch" mode.

EXAMPLES

In the examples described below, the abbreviation "SC" denotes the solids content, which is measured according to the standard ASTM E1756-08(2015) "Standard Test Method for Determination of Total Solids in Biomass".

Example 1 (Comparative)

This example relates to a process for impregnating and pretreating wood, having the following features:
Feedstock: Poplar wood, flow rate 6.79 tonnes/hour, solids content SC: 55.6%, mean composition (SC basis):

|  | % (SC basis) |
| --- | --- |
| Cellulose | 42.6% |
| Hemicellulose | 20.5% |
| Lignin and others (ash, extractable matter, etc.) | 36.9% |

The wood is used in the form of chips with a characteristic size of 50 mm. The temperature of the chips entering the unit is room temperature.

The chips are conveyed to the impregnation reactor 5 via the conical screw 6a. The impregnation reactor 5 is a vertical tube in which the biomass 6b is conveyed vertically by two counter-rotating screws 5c in series. The total working volume of the reactor is 1.95 m$^3$. The screw speed and the level of liquid are regulated so as to ensure a residence time of 30 seconds in the immersed zone and a draining time of 60 seconds.

The following are introduced into the impregnation reactor 5:
the compressed wood chips, via the conical transfer screw 6a
2.5 tonnes/hour of an acidic liquor prepared with water and sulfuric acid at a mass concentration of 1.76% by weight, at a temperature of 90° C.
0.3 tonnes/hour of water introduced into the bottom of the impregnation reactor 5 in the zone 5d to lubricate the vertical transportation screws 5c, at a temperature of 20° C.

The impregnated chips are removed from the impregnation reactor 5 and transferred to the steam explosion reactor 9. The steam explosion pretreatment is performed at 200° C. in a continuous configuration described above and using a short residence time. The medium is abruptly expanded to a pressure of 1.3 atm.

The pretreated substrate thus obtained has a free xylose content of 6.9% of xylose (SC basis) and a potential xylose content (monomer, oligomers and polymers) of 14.5% expressed in the form of xylose (SC basis). The impregnation consumed 44 kg of pure H$_2$SO$_4$/hour, i.e. 11.65 kg of pure acid/tonne of substrate SC. The degree of xylose release, expressed as the percentage of xylose in free form relative to the total potential xylose, is 47.6%.

Example 2 (According to the Invention)

This example uses a process of impregnation according to the invention and of pretreatment of wood, treating the same feedstock as in example 1.

The chips are conveyed to the impregnation reactor 5 via the conical screw 6a. The impregnation reactor 5 is the same as in example 1. The speed of the screws 5c and the level of liquid are regulated so as to ensure a residence time of 30 seconds in the immersed zone and a draining time of 60 seconds. The following are introduced into the impregnation reactor 5:
the compressed wood chips, via the conical transfer screw 6a
2.5 tonnes/hour of an acidic liquor prepared with water and sulfuric acid at a mass concentration of 1.57% by weight, at a temperature of 85° C., via an inlet located in the impregnation zone 5a
0.3 tonnes/hour of the same acidic liquor is introduced into the bottom of the impregnation reactor 5; in the zone 5d under the point of injection of the biomass into the reactor 6, at a temperature of 85° C.

The impregnated chips are removed from the impregnation reactor 5 and are continuously transferred to a steam explosion reactor 9 via the feed screw 8. The steam explosion pretreatment is performed in the same manner as for comparative example 1.

The pretreated substrate thus obtained has a free xylose content of 11.1% of xylose (SC basis) and a potential xylose content (monomer, oligomers and polymers) of 15.1% expressed in the form of xylose (SC basis). The impregnation consumed 44 kg of pure H$_2$SO$_4$/hour, i.e. 11.65 kg of pure acid/tonne of substrate SC. The degree of xylose release, expressed as the percentage of xylose in free form relative to the total potential xylose, is 73.5%.

No precise and robust measurement of the quality of impregnation of the biomass with the liquor exiting the impregnation step exists, but this quality can be assessed, indirectly, by means of the xylose content obtained at the end of the steam explosion pretreatment in the reactor 9 according to FIG. 2. It should be noted that the advantages of the invention are also preserved if the impregnation step and the steam explosion pretreatment step are performed discontinuously, in "batch" mode.

By comparing the results of examples 1 and 2, it is seen, in addition, that the invention, by also injecting liquor into the bottom of the reactor, made it possible to obtain much better release of xylose into the pretreated substrate, all the factors being otherwise equal, thus demonstrating better impregnation of the biomass, for an identical acid consumption: the value notably passes from 6.9% of free xylose content to 11.1% of free xylose content, which means that, with the invention, almost twice as much xylose is able to be released from the same biomass without consuming more acid, with a modification in the process and the equipment that is entirely modest and easy to implement with the means existing on the production line.

Example 3 (According to the Invention)

In this example, it is straw that is treated with the process for converting lignocellulosic biomass into ethanol according to the invention. The straw used has the following features: Feedstock: Native straw, flow rate 3.36 tonnes/hour, solids content SC: 85.6%, mean composition (SC basis):

|  | % (SC basis) |
|---|---|
| Cellulose | 36.0% |
| Hemicellulose | 26.8% |
| Lignin and others (ash, extractable matter, etc.) | 37.2% |

The straw is milled on a 50 mm screen and then conveyed to the impregnation reactor 5 by the conical screw 6a. The following are introduced into the impregnation reactor 5:
the compressed straw, via the conical transfer screw 6a
14.53 tonnes/hour of an acidic liquor prepared in the acidic liquor preparation tank 3, at a temperature of 75° C.
0.57 tonnes/hour of this same acidic liquor introduced into the bottom of the impregnation reactor at a temperature of 75° C., in the zone 5d under the point of introduction of the biomass into the reactor.

The impregnated straw is removed from the impregnation reactor 5 and transferred to a conical transfer screw 8 which ensures its introduction into a steam explosion reactor 9. During the passage of the impregnated straw into the conical transfer screw, a juice known as the press liquor is extracted, at a mean flow rate of 9.74 tonnes/hour, this press liquor being mixed with the water for the external washing of the conical screw, the total flow rate collected being 10.59 tonnes/hour, 85% of which is recycled. The steam explosion pretreatment is performed at 185° C. in a continuous configuration using a short residence time. The medium is abruptly expanded to a pressure of 1.3 atm.

The acidic liquor sent to the impregnation reactor is prepared in an acidic liquor tank by mixing:
the partially recycled press liquor, at a flow rate of 9 tonnes/hour
a supply of $H_2SO_4$ acid at 96% by weight, at a flow rate of 0.126 tonnes/hour
a supply of water at a flow rate of 5.973 tonnes/hour The press liquor 10 is extracted from the feed screw of the pretreatment explosion reactor 9 and, in this example, it is collected and pumped to the liquor preparation tank 3 to be recycled therein. The mixing tank 3 is thus fed here by a water supply pipe 1, a pipe 2 for supplying concentrated $H_2SO_4$ acid solution, and an additional pipe conveying the recycled press liquor 10 (not shown in the figures).

The pretreated substrate thus obtained has a free xylose content of 15.9% of xylose (SC basis) and a potential xylose content (monomer, oligomers and polymers) of 21.8% expressed in the form of xylose (SC basis).

The pretreated substrate is then sent to the reactor 16 for simultaneous enzymatic hydrolysis and fermentation. To achieve the desired operating conditions, a stream of enzymatic cocktail, a yeast stream and a water stream are added to the substrate, for a total of 4.85 tonnes/hour. The enzymatic cocktail was produced by a fungus *Trichoderma reesei*, and the yeast used is a yeast of the type *Saccharomyces cerevisiae* genetically modified to consume xylose. At the end of the reaction, the medium contains ethanol at a concentration of 47 g/kg. The wine 19 is sent into a separation unit 20 making it possible to obtain a stream of ethanol at a concentration of 99.7% by weight by distillation and dehydration. This ethanol stream has a flow rate of 0.552 tonnes/hour.

The injection of additional liquor into the bottom of the impregnation reactor is also efficient for biomasses of straw type.

The invention claimed is:
1. A process for treating a lignocellulosic biomass (6), said process comprising the following steps:
   a. preparing an impregnation liquor (4) containing a chemical catalyst intended for the impregnation of the biomass, selected from the group consisting of an acid catalyst, a basic catalyst and an oxidizing catalyst,
   b. introducing milled biomass via an inlet of an impregnation reactor (5), said inlet being located in a first impregnation zone (5a) of said impregnation reactor wherein said impregnation reactor comprises two superposed zones which are said first impregnation zone and a second "draining" zone (5b) positioned above the impregnation zone,
   c. introducing a first portion of the liquor (4) via a first liquor inlet located in said first impregnation zone (5a) of the reactor, and
   d. introducing a second portion of said liquor into said reactor (5) via a second liquor inlet in another reactor zone (5d) located below a biomass inlet (6) located in the first impregnation zone (5b),
   e. transferring the impregnated and drained biomass from a reactor draining zone outlet (5) to a cooking pretreatment reactor (9),
   f. pretreating said impregnated and drained biomass in said cooking reactor (9), and
   g. conducting enzymatic hydrolysis (16) of the pretreated biomass (15).

2. The process as claimed in claim 1, wherein the biomass (6) is transported from the first impregnation zone (5a) to the second draining zone (5b) by one or more transportation screws (5c), the biomass being impregnated with the liquor (4) in the first zone and being drained in the second zone.

3. The process as claimed in claim 1, wherein the introduction of the biomass (6) into the first impregnation zone (5a) of the reactor is performed by a feeder (6a) creating a biomass plug (6b) which prevents backflow of any liquid from said first zone (5a) into said feeder (6a).

4. The process as claimed in claim 1, wherein 80% to 98%, of the liquor introduced into the impregnation reactor (5) is introduced via the first liquor inlet (4a), and the remainder of the liquor is introduced into the reactor via the second liquor inlet (4b).

5. The process as claimed in claim 1, wherein the introduction of liquor via the first liquor inlet (4a) and via the second liquor inlet (4b) takes place continuously or discontinuously.

6. The process as claimed in claim 1, wherein an impregnation reactor zone (5d) of the reactor (5) in which the second liquor inlet is located, is an inactive zone located at a bottom of the reactor positioned substantially vertically or obliquely relative to the vertical.

7. The process as claimed in claim 1, additionally comprising,
adjusting the pH of the liquor to between 0.1 and 4 and wherein the liquor (4) is an acid catalysis liquor.

8. A facility for treating a lignocellulosic biomass, comprising:
- a zone (3) for preparing an impregnation liquor (4) containing a chemical catalyst for the impregnation of the biomass, chosen from an acid, basic or oxidizing catalyst, and equipped with a liquor outlet;
- an impregnation reactor (5) comprising a first impregnation zone (5a) equipped with a biomass inlet and a second zone superposed on the first, wherein the second zone is a draining zone (5b), and equipped with a biomass outlet;
- a milled biomass feeder (6a) to the impregnation reactor (5) via the biomass inlet of the reactor located in the first impregnation zone (5a);
- a first impregnation liquor feeder (4a) to the reactor (5) connecting a liquor outlet of the liquor (4) preparation zone (3) to a first liquor inlet in the first impregnation zone of the reactor; and
- a second impregnation liquor feeder (4b) to the reactor (5) connecting a liquor outlet of the liquor preparation zone (3) to a second liquor inlet in a reactor zone (5d) located below the biomass inlet of the first impregnation zone (5a);
- a cooking pretreatment reactor (9) which receives impregnated and drained biomass from a reactor draining zone outlet (5) and pretreats said impregnated and drained biomass, and an enzymatic hydrolysis reactor (16) which receives the pretreated biomass (15).

9. The process of claim 1 for the treatment of the biomass (6), wherein said treatment results in the production of sugars, biofuels or biobased molecules.

10. The process of claim 1, wherein the chemical catalyst is an acid catalyst.

11. The process as claimed in claim 1, additionally comprising adjusting the pH of the liquor to between 0.3 and 2.

12. The process as claimed in claim 1, wherein 85% to 90% of the liquor introduced into the impregnation reactor (5) is introduced via the first liquor inlet.

13. A process of claim 1, additionally comprising: a step of h. alcoholic fermentation (18) of enzymatic hydrolysis must (17) obtained from the enzymatic hydrolysis of the pretreated biomass.

14. The facility as claimed in claim 8, wherein the impregnation reactor (5) is of vertical or oblique orientation relative to the vertical, the biomass undergoing an ascending motion from the first impregnation zone (5a) to the second draining zone (5b) by one or more transportation screws (5c) wherein said one or more transportation screws are placed in the reactor connecting said zones.

15. The facility as claimed in claim 8, wherein the liquor preparation zone (3) is a tank or a static mixer or a dynamic mixer.

16. The facility as claimed in claim 8, wherein the first and the second liquor feeders comprise a common pipe portion (4) connected to the same liquor outlet of the liquor preparation zone (3) or are each connected to a different outlet of the liquor preparation zone (3).

17. The facility as claimed in claim 8, wherein the biomass feeder (6a) creates a biomass plug (6b) which prevents the backflow of any liquid from said first zone into said biomass feeder, wherein said biomass feeder is a feed screw.

18. The facility as claimed in claim 8, additionally comprising:
- an alcoholic fermentation reactor (18) positioned downstream from the enzymatic hydrolysis reactor, wherein at least two of the reactors, are mounted in series.

19. The process of claim 8, wherein the chemical catalyst is an acid catalyst.

20. A process for treating a lignocellulosic biomass (6), said process comprising the following steps:
- a. preparing an impregnation liquor (4) containing a chemical catalyst intended for the impregnation of the biomass, selected from the group consisting of an acid catalyst, a basic catalyst and an oxidizing catalyst,
- b. introducing milled biomass via an inlet of an impregnation reactor (5), said inlet being located in a first impregnation zone (5a) of said impregnation reactor wherein said impregnation reactor comprises two superposed zones which are said first impregnation zone and a second "draining" zone (5b) positioned above the impregnation zone,
- c. introducing a first portion of the liquor (4) via a first liquor inlet located in said first impregnation zone (5a) of the reactor, and
- d. introducing a second portion of said liquor into said reactor (5) via a second liquor inlet in another reactor zone (5d) located below a biomass inlet (6) located in the first impregnation zone (5b)
- e. transferring the impregnated and drained biomass from a reactor draining zone outlet (5) to a cooking pretreatment reactor (9), and
- f. pretreating said impregnated and drained biomass in said cooking reactor (9).

\* \* \* \* \*